(12) United States Patent
Hung et al.

(10) Patent No.: US 10,140,536 B2
(45) Date of Patent: Nov. 27, 2018

(54) FINGERPRINT IDENTIFICATION APPARATUS AND BIOMETRIC SIGNALS SENSING METHOD USING THE SAME

(71) Applicant: GINGY TECHNOLOGY INC., Hsinchu (TW)

(72) Inventors: Chun-Lang Hung, Hsinchu (TW); Tsung-Shan Chen, Hsinchu (TW)

(73) Assignee: GINGY TECHNOLOGY INC., Hsinchu (TW)

(*) Notice: Subject to any disclaimer, the term of this patent is extended or adjusted under 35 U.S.C. 154(b) by 70 days.

(21) Appl. No.: 15/364,397

(22) Filed: Nov. 30, 2016

(65) Prior Publication Data

US 2017/0083779 A1 Mar. 23, 2017

Related U.S. Application Data

(63) Continuation-in-part of application No. 14/835,130, filed on Aug. 25, 2015, which is a
(Continued)

(30) Foreign Application Priority Data

| Aug. 26, 2014 | (TW) | 103129359 A |
| Dec. 22, 2014 | (TW) | 103144744 A |
| Sep. 7, 2016 | (TW) | 105128937 A |

(51) Int. Cl.
*G06K 9/00* (2006.01)
*A61B 5/00* (2006.01)
(Continued)

(52) U.S. Cl.
CPC ........ *G06K 9/00892* (2013.01); *A61B 5/1172* (2013.01); *A61B 5/1455* (2013.01);
(Continued)

(58) Field of Classification Search
None
See application file for complete search history.

(56) References Cited

U.S. PATENT DOCUMENTS

| 9,770,199 B2* | 9/2017 | Hung | A61B 5/1172 |
| 2006/0179939 A1* | 8/2006 | Duval | G01D 11/245 73/431 |

(Continued)

*Primary Examiner* — Mohammad J Rahman
(74) *Attorney, Agent, or Firm* — Li & Cai Intellectual Property (USA) Office

(57) ABSTRACT

This invention disclosures a fingerprint identification apparatus and biometric signals sensing method using the same. The fingerprint identification apparatus comprises: a photoelectric sensor, a light module and an identification unit in which the photoelectric sensor with a fingerprint sensing face is to transform light intensity signals into electronic signals; the light module is to produce test light; the identification unit is electrically connected with the photoelectric sensor, wherein, there are different sensing modes with corresponding actions; in the first sensing mode, the identification unit senses a fingerprint image by the photoelectric sensor; in the second mode, the identification unit senses a spectrum by the photoelectric sensor to determine the blood glucose information. Therefore, this fingerprint identification apparatus can detect the fingerprint and blood glucose at the same time.

16 Claims, 6 Drawing Sheets

Related U.S. Application Data continuation-in-part of application No. 15/208,619, filed on Jul. 13, 2016, which is a continuation-in-part of application No. 14/978,237, filed on Dec. 22, 2015, now Pat. No. 9,770,199.

(51) Int. Cl.
| | | |
|---|---|---|
| *A61B 5/1455* | (2006.01) | |
| *A61B 5/1172* | (2016.01) | |
| *A61B 5/145* | (2006.01) | |
| *G06K 9/20* | (2006.01) | |
| *H04N 5/30* | (2006.01) | |

(52) U.S. Cl.
CPC ........ *A61B 5/14532* (2013.01); *A61B 5/6826* (2013.01); *G06K 9/00013* (2013.01); *G06K 9/00087* (2013.01); *G06K 9/2018* (2013.01); *G06K 2009/0006* (2013.01); *G06K 2009/00932* (2013.01); *H04N 5/30* (2013.01)

(56) References Cited

U.S. PATENT DOCUMENTS

| | | | | |
|---|---|---|---|---|
| 2006/0228897 | A1* | 10/2006 | Timans | H01L 21/67115 438/758 |
| 2007/0027374 | A1* | 2/2007 | Wihlborg | A61B 5/14532 600/322 |
| 2007/0030475 | A1* | 2/2007 | Rowe | A61B 5/117 356/71 |
| 2007/0086629 | A1* | 4/2007 | Drews | G06K 9/00026 382/124 |
| 2011/0007951 | A1* | 1/2011 | Mil'shtein | G06K 9/00033 382/124 |
| 2011/0200237 | A1* | 8/2011 | Nakamura | A61B 5/1171 382/127 |
| 2015/0062319 | A1* | 3/2015 | Higuchi | A61B 5/1171 348/77 |
| 2015/0130917 | A1* | 5/2015 | Mil'shtein | G06K 9/00033 348/77 |

\* cited by examiner

FINGERPRINT IDENTIFICATION APPARATUS AND BIOMETRIC SIGNALS SENSING METHOD USING THE SAME

CROSS-REFERENCE TO RELATED APPLICATION

This application is a Continuation of U.S. patent application Ser. No. 14/835,130 filed on Aug. 25, 2015, Ser. No. 14/978,237 filed on Dec. 22, 2015, and Ser. No. 15/208,619 filed on Jul. 13, 2016. This patent application identified above is incorporated here by reference in its entirety to provide continuity of disclosure, and this application also claims the priority to Taiwan Patent Application No. 105128937 filed in the Taiwan Patent Office on Sep. 7, 2016, and the entirety of each of the above-mentioned patent applications is hereby incorporated by reference herein and made a part of this specification.

BACKGROUND

1. Technical Field

The present disclosure relates to a fingerprint identification apparatus, in particular, to a fingerprint identification apparatus and biometric signals sensing method using the same.

2. Description of Related Art

Capacitive fingerprint sensors and optical fingerprint sensors are well known in the technical field of fingerprint identification. Generally, the capacitive fingerprint sensor is miniaturized for use on handheld devices, but its durability and sensitivity are gradually diminished as the chip is exposed to the outside and the capacitive fingerprint sensor may be affected by sweat and other external factors. As to the optical fingerprint sensor, it has been well developed, but optical elements are necessary for an optical fingerprint sensor, causing an optical fingerprint sensor to be hard to apply to handheld devices because of a bulky volume.

Capacitive fingerprint sensors are made by semiconductor manufacturing process. The capacitive structure and capacitive sensing circuit are integrated within a chip in which the capacitive sensing units are distributed in a high density for sensing fingerprint images. When a finger presses on the chip face, the distance difference between the fingerprint valleys and the fingerprint peaks of the finger and the capacitive sensing units may produce different capacitance values which are used to form a fingerprint image.

Optical fingerprint sensors are mainly formed of a light source, a dispersive prism, and a charge-coupled device (CCD). When a finger presses the dispersive prism, a fingerprint image could be obtained based on the absorption of the total reflection by the fingerprint valleys and the fingerprint peaks of the finger. The CCD can extract the fingerprint valleys and the fingerprint peaks of the finger to form the fingerprint image. As the finger is pressed upon optical elements, the optical fingerprint sensors could be relatively cost-effective and durable. Thus, the optical fingerprint sensors have been widely used in public places.

However, capacitive fingerprint sensors and optical fingerprint sensors are mainly used to sense fingerprint images, and neither of them can simultaneously sense fingerprint images and biometric signals. Different biometric signals need to be sensed by using different sensing techniques, but the sensing techniques cannot integrate capacitive fingerprint sensors and optical fingerprint sensors.

SUMMARY

The primary purpose of the present disclosure is to provide a fingerprint identification apparatus and biometric signals sensing method using the same which is adapted to sense fingerprint images and biometric signals such as blood glucose information. In addition, there are different sensing modes with corresponding actions, wherein in the first sensing mode, the identification unit senses a fingerprint image by the photoelectric sensor, and in the second mode, the identification unit senses a spectrum by the photoelectric sensor to determine blood glucose information. Therefore, the present disclosure can detect the fingerprint and blood glucose at the same time.

According to one exemplary embodiment of the present disclosure, a fingerprint identification apparatus adapted to sense fingerprint images and blood glucose information is provided, including a photoelectric sensor, a light module and an identification unit. The photoelectric sensor has a fingerprint sensing face used to transform light intensity signals into electronic signals. The light module is to generate test light to the finger. The identification unit is electrically connected with the photoelectric sensor. There are different sensing modes with corresponding actions, wherein in the first sensing mode, the identification unit senses a fingerprint image by the photoelectric sensor, and in the second mode, the identification unit senses a spectrum by the photoelectric sensor to determine blood glucose information.

According to an exemplary embodiment of the invention, the light module is disposed around the photoelectric sensor.

In a preferred exemplary embodiment, the light module is disposed on the photoelectric sensor and an accommodating space for accommodating the finger is disposed between the photoelectric sensor and the light module.

According to an exemplary embodiment of the invention, the light module comprises a plurality of light sources having different wavelength ranges for generating the test light, and the test light has a wavelength range ranging from 700 nm-3000 nm.

According to an exemplary embodiment of the invention, the light module comprises the plurality of light sources and a plurality of filters, and the plurality of filters are respectively disposed on the plurality of light sources for producing a spectrum having different wavebands.

According to an exemplary embodiment of the invention, in the second sensing mode, the light module sequentially generates test light having different wavelength ranges, and the test light has a wavelength range ranging from 700 nm-3000 nm.

According to an exemplary embodiment of the invention, the photoelectric sensor has a sensing array disposed below the fingerprint sensing face, a part of the sensing array is set as a spectrum sensing region, and the identification unit senses the spectrum information through the spectrum sensing region.

According to an exemplary embodiment of the invention, the photoelectric sensor has the sensing array and a spectrum sensing element, the sensing array is used to sense the fingerprint image, and the spectrum sensing element is used to sense the spectrum information.

According to an exemplary embodiment of the invention, the fingerprint identification apparatus verifies user data according to the fingerprint image, and determines a relationship between the blood glucose information and user according to the user data.

According to an exemplary embodiment of the invention, the fingerprint identification apparatus verifies whether the finger is real or not according to the spectrum information.

According to an exemplary embodiment of the invention, the photoelectric sensor comprises the sensing array formed of a plurality of photosensitive units, and each of the plurality of photosensitive units comprises a first type doped semiconductor layer and a second type doped semiconductor layer.

According to an exemplary embodiment of the invention, the identification unit comprises an analog/digital converter and a processing unit. The analog/digital converter is electrically connected to the photoelectric sensor for receiving the electronic signals outputted by the photoelectric sensor and converting the electronic signals into digital signals. The processing unit is electrically connected to the analog/digital converter and receives the digital signals to calculate the blood glucose information.

According to an exemplary embodiment of the invention, the fingerprint identification apparatus further includes a light controller electrically connected to the light module for controlling the spectrum of the test light.

According to another exemplary embodiment of the present disclosure, a biometric signals sensing method adapted to a fingerprint identification apparatus is provided, including: sensing a fingerprint image by a photoelectric sensor; verifying user data according to the fingerprint image; sensing spectrum information by the photoelectric sensor; calculating blood glucose information according to the spectrum information, and obtaining a relationship between the blood glucose information and the user data.

According to an exemplary embodiment of the invention, the biometric signals sensing method further includes: verifying whether a sensed finger is a real finger according to the spectrum information.

According to an exemplary embodiment of the invention, in the step of sensing the spectrum information by the photoelectric sensor further comprises: providing test light having different spectra to the sensed finger, wherein the test light is generated on or below the finger.

To sum up, the fingerprint identification apparatus and biometric signals sensing method using the same provided by the present disclosure use a photoelectric sensor to sense a fingerprint image or spectrum information, a light module to generate a test light having different wavelengths to a finger, and an identification unit to obtain the fingerprint image or the spectrum information so as to recognize a fingerprint or to determine biometric signals such as blood glucose information. In addition to sensing fingerprint image, the present disclosure is capable of sensing other biometric signals. The fingerprint identification apparatus of the present disclosure has a small size and can integrate biometric signals such as blood glucose information with the sensing technique, thereby simultaneously sensing various biometric signals and verifying user data. Thus, the present disclosure effectively promotes usability and saves the operation time.

In order to further understand the techniques, means and effects of the present disclosure, the following detailed descriptions and appended drawings are hereby referred to, such that, and through which, the purposes, features and aspects of the present disclosure can be thoroughly and concretely appreciated; however, the appended drawings are merely provided for reference and illustration, without any intention to be used for limiting the present disclosure.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DESCRIPTION OF THE EXEMPLARY EMBODIMENTS

Figure 1:
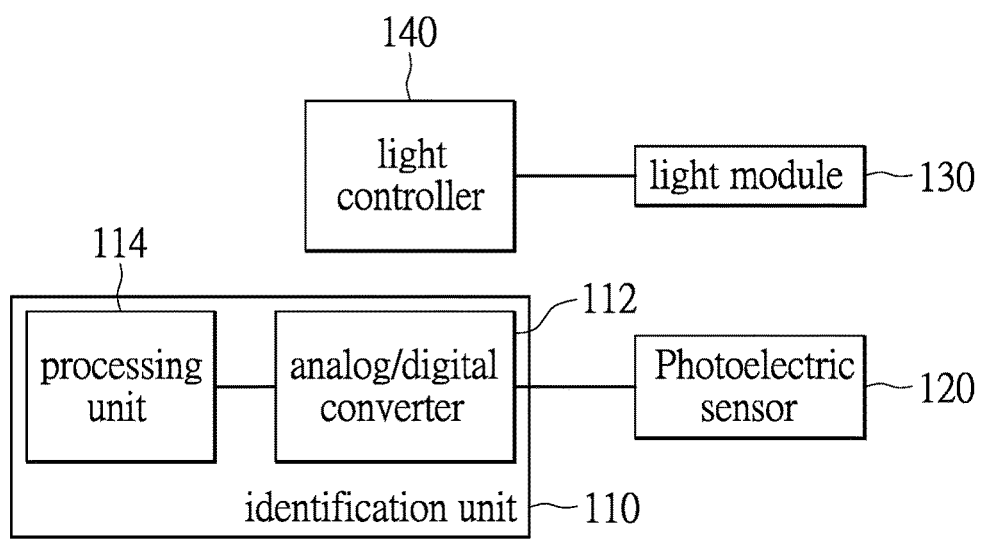
FIG. 1 is a function block diagram of one embodiment of the fingerprint identification apparatus of the present disclosure.

Reference will now be made in detail to the exemplary embodiments of the present disclosure, examples of which are illustrated in the accompanying drawings. Wherever possible, the same reference numbers are used in the drawings and the description to refer to the same or like parts.

Figure 2A:
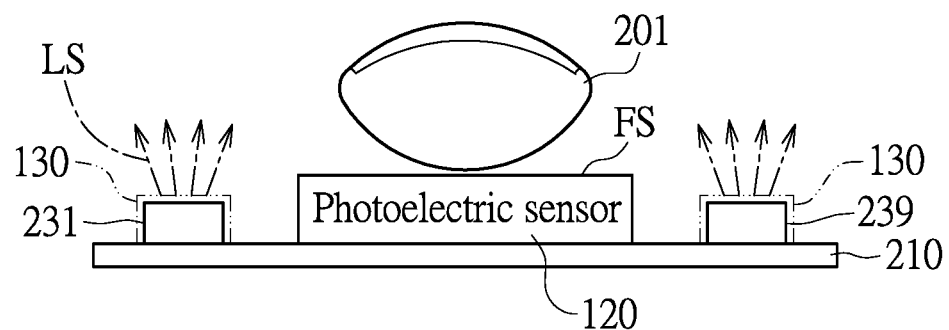
FIG. 2A is a schematic diagram illustrating the structure of one embodiment of the fingerprint identification apparatus of the present disclosure.
Figure 2B:
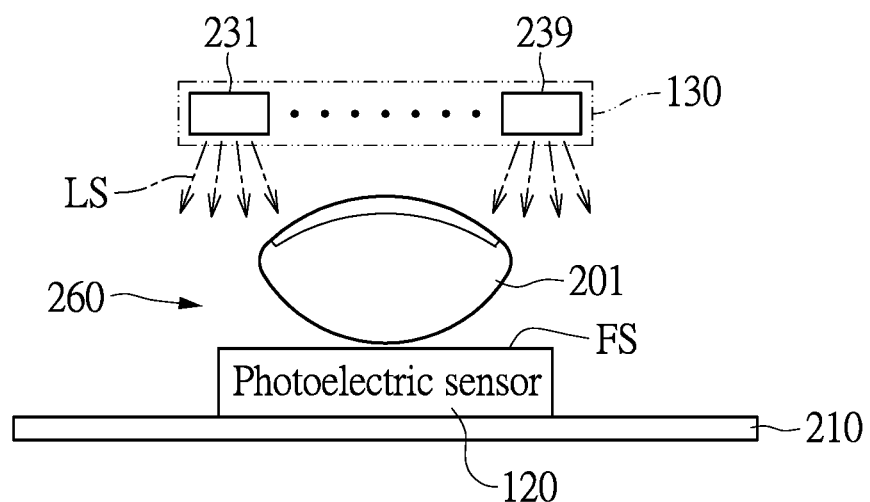
FIG. 2B is a schematic diagram illustrating the structure of the other embodiment of the fingerprint identification apparatus of the present disclosure.

Please refer to FIG. 1, FIG. 2A and FIG. 2B together, which are respectively a function block diagram of one embodiment of the fingerprint identification apparatus of the present disclosure, a schematic diagram illustrating the structure of one embodiment of the fingerprint identification apparatus of the present disclosure and a schematic diagram illustrating the structure of another embodiment of the fingerprint identification apparatus of the present disclosure. As shown in FIG. 1, the fingerprint identification apparatus 100 includes an identification unit 110, at least one photoelectric sensor 120, at least one light module 130 and a light controller 140. The identification unit 110 includes an analog/digital converter 112 and a processing unit 114, wherein the analog/digital converter 112 is electrically connected to the photoelectric sensor 120 and the processing unit 114. The light controller 140 is electrically connected to the light module 130 for controlling a wavelength range of a test light LS emitted by the light module 130.

The photoelectric sensor 120 and the light module 130 are disposed on the same surface of a substrate 210, wherein the light module 130 is formed of a plurality of light sources 231-239 and disposed around the photoelectric sensor 120. The light sources 231-239 may be LEDs, and the present disclosure is not limited thereto. A surface of the photoelectric sensor 120 has a fingerprint sensing surface FS on which a finger 201 presses to be sensed. The photoelectric sensor 120 is formed by the semiconductor packaging technology, and housing of the photoelectric sensor 120 is packaged by a resin and a surface of the housing has no opening In addition, a surface of the package structure can be used as the fingerprint sensing surface FS for sensing the finger 201. Please refer to FIG. 2B which is a schematic diagram illustrating the structure of the other embodiment of the fingerprint identification apparatus of the present disclosure. In the present embodiment, the photoelectric sensor 120 and the light module 130 are disposed opposite to each other, wherein the light module 130 is disposed on the photoelectric sensor 120. An accommodating space 260 is disposed between the photoelectric sensor 120 and the light module 130 for accommodating the finger 201 to be sensed. The plurality of light sources 231-239 respectively generate the test light LS having its own wavelength range. The light module 130 can be selectively disposed at the same side of or on the photoelectric sensor 120 according to the light transmittance of an object to be sensed.

When executing the sensing, the light module 130 emits the test light LS to the finger 201, the photoelectric sensor 120 receives light intensity signals and then transforms them into electronic signals such as photocurrent signals. The analog/digital converter 112 receives the sensing signals outputted by the photoelectric sensor 120, and transforms them into digital signals and then transmits the digital signals to the processing unit 114 for calculating and analyzing, thereby obtaining a fingerprint image or blood glucose information.

In the present embodiment, the fingerprint identification apparatus 100 has two sensing modes with corresponding actions, wherein a first sensing mode is to sense a fingerprint image, and a second sensing mode is to sense spectrum information and then to determine blood glucose information according to the spectrum information. In the first sensing mode, the identification unit 110 produces a fingerprint image according to the light intensity caused by the distance difference between the fingerprint valleys and the fingerprint peaks of the finger 201 and the fingerprint sensing surface FS. In the second sensing mode, the light module 130 generates the test light LS having different light spectra (wavelength range) to the finger 201, and the photoelectric sensor 120 senses the light intensity reflected or transmitted from the finger 201 to produce the spectrum information such as infrared absorption spectrum. The light module 130 generates light having different wavelength ranges by using the plurality of light sources 231-239, wherein the wavelength range is between 700 nm-3000 nm which includes the infrared wavelength range (0.78-3μ). When sensing biometric signals, the light module 130 sequentially generates the test light LS having different spectra to the finger 201 to sense the finger 201. According to the output sequence of the spectra, the fingerprint identification apparatus 100 can obtain the complete spectrum information to determine the biometric signals.

As specific substances in human tissue and blood have the absorption characteristics in a specific spectrum, the absorption spectrum information such as wavenumber of absorbance and absorbance index can be used to calculate and analyze the characteristics and quantity of the specific substances. The infrared spectroscopy is used in the present embodiment, but the present disclosure is not limited thereto. In the present exemplary embodiment, an atom in a molecule can absorb energy when it is in vibrational-rotational transitions and the specific functional group has a specific absorption band which is not changed by the external environment, and detecting the absorption spectrum senses the specific functional group, thereby determining biometric signals such as blood glucose level. According to the wavenumbers, the absorption spectrum is divided into three regions, wherein 14290-4000 $cm^{-1}$ belongs to the near infrared region, 4000-666 $cm^{-1}$ is the middle infrared region, and 600-100 $cm^{-1}$ presents the far infrared region.

The near infrared region is associated with the absorption of the overtone and the combination band of atom, and the far infrared region is related to the absorption with respect to the molecular rotation and metal bond.

For example, the infrared absorption wavenumber of water molecule is about 3657 $cm^{-1}$ and 3766 $cm^{-1}$. In wood spirit, the C—O stretching frequency is 1034 $cm^{-1}$ (9.67 μm); ethanol has the stretching frequency of 1053 $cm^{-1}$ (9.50 μm), and 2-Butanol is of 1105 $cm^{-1}$ (9.05 μm). The characteristic absorption peak of polysaccharide is 3401 $cm^{-1}$ (O—H), 2919 $cm^{-1}$ (C—H), 1381 $cm^{-1}$ and 1076 $cm^{-1}$ (C—O). The absorption peak at 900 $cm^{-1}$ points to the polysaccharide being connected by a β-glycosidic bond. There is a clear absorption peak of a protein in the N—H deformation vibration 1650-1550 $cm^{-1}$, showing that the sample is a polysaccharide-protein complex. Generally, fat has an absorption wavelength ranging from 900 nm-950 nm, the water molecule has an absorption wavelength ranging from 900 nm-1000 nm, and protein has an absorption wavelength ranging from 1000 nm-1050 nm In the near infrared region, the absorption spectrum of macromolecules such as water and proteins overlaps that of blood glucose to make the absorption peak value and the wavelength position drift. Thus, the process of analyzing and calculating has to choose a better calculation and process model to rule out the interference caused by the macromolecule so as to increase the sensing effect. The wavenumber of the absorption spectrum mentioned above is used as an example, and the present disclosure is not limited thereto. The statistics varies with different sensing methods.

After calculating and analyzing the spectrum information obtained from the photoelectric sensor 120, the fingerprint identification apparatus 100 can obtain the blood glucose information. The calculation method includes infrared absorption spectrum, analysis of variance, regression analysis, curve fitting, and so on, and the present disclosure is not limited thereto. However, different sensing methods sense an object by using a spectrum having different wavebands, and the present disclosure is not limited thereto. The fingerprint identification apparatus 100 can output a spectrum having specific waveband to sense a specific object, and the present disclosure does not limit the outputted waveband. In addition, in the present embodiment, the peak separation method and differential spectroscopic method are used to analyze spectrum, and the present disclosure is not limited thereto.

The fingerprint identification apparatus 100 verifies user data by using the fingerprint image obtained from the first sensing mode, and verifies the biometric signals such as blood glucose level by using the spectrum information obtained from the second sensing mode, so that the fingerprint identification apparatus 100 can determine a relationship between the blood glucose level and the user to produce the blood glucose information related to the user, thereby monitoring the user's blood glucose level or applying it to a cloud medical application.

In addition, the fingerprint identification apparatus 100 recognizes whether the finger 201 is a real finger through the second sensing mode. Because a fake finger has physiological features and absorption characteristics differing from a real one, it can use the infrared absorption spectrum to determine whether it is a real finger or not. For example, as a fake finger does not have glucose and bone, it can determine the authenticity of the finger by whether its absorption spectrum includes the absorption peak of glucose and bone.

Figure 3A:
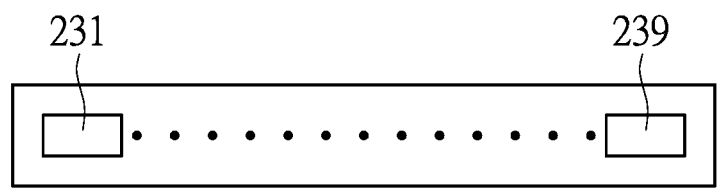
FIG. 3A is a schematic diagram of one embodiment of the light module of the present disclosure.
Figure 3B:
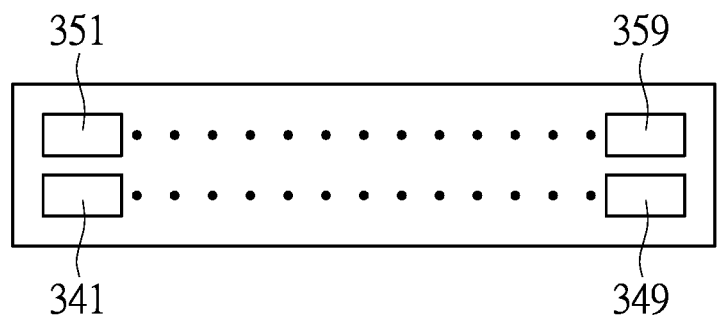
FIG. 3B is a schematic diagram of the other embodiment of the light module of the present disclosure.

The present paragraph describes elements of the fingerprint identification apparatus 100. The light controller 140 is electrically connected to the light module 130 for supplying power and controlling the plurality of light sources 231-239 to adjust the wavelength range of the test light LS emitted by the light module 130. The light module 130 has two embodiments which are respectively shown in FIG. 3A and FIG. 3B, wherein FIG. 3A is a schematic diagram of one embodiment of the light module of the present disclosure, and FIG. 3B is a schematic diagram of another embodiment of the light module of the present disclosure. As shown in FIG. 3A, the light module 130 includes the plurality of light sources 231-239 having their respective spectral ranges for generating light having the specific waveband ranging from 700 nm-3000 nm. For example, the light source 231 is a GaAs light source and its central wavelength is 830 nm-950 nm, but the present disclosure is not limited thereto. The light module 130 can select one or more of the plurality of light sources 231-239 to generate the necessary spectrum.

Please refer to FIG. 3B. The light module 130 is formed of a plurality of light sources 341-349 having all waveband spectra and a plurality filters 351-359 covering the plurality of light sources 341-349. The plurality of light sources 341-349 having all waveband spectra have a wider spectral region such as 700 nm-3000 nm, and the plurality of filters 351-359 can select wavelength and filter lights without having specific wavelength. For example, if the filter 351 has a waveband of 700 nm-800 nm, lights emitted by the light source 341 cannot transmit through the filter 351, except for the light having the wavelength of 700 nm-800 nm. If the filter 359 has a waveband of 700 nm-2800 nm, when lights emitted by the light source 349 enter the filter 359, only the light having the wavelength of 2700 nm-2800 nm can transmit therethrough. In other words, by selecting the plurality of filters 351-359 having their respective wavebands, a light array 131 can produce a spectrum having different wavebands, thereby generating the test light LS having the desired waveband range. The light source having all waveband spectra mentioned above may be a halogen lamp or a solid-state light emitting element such as an LED, but the present disclosure is not limited thereto.

Figure 4A:
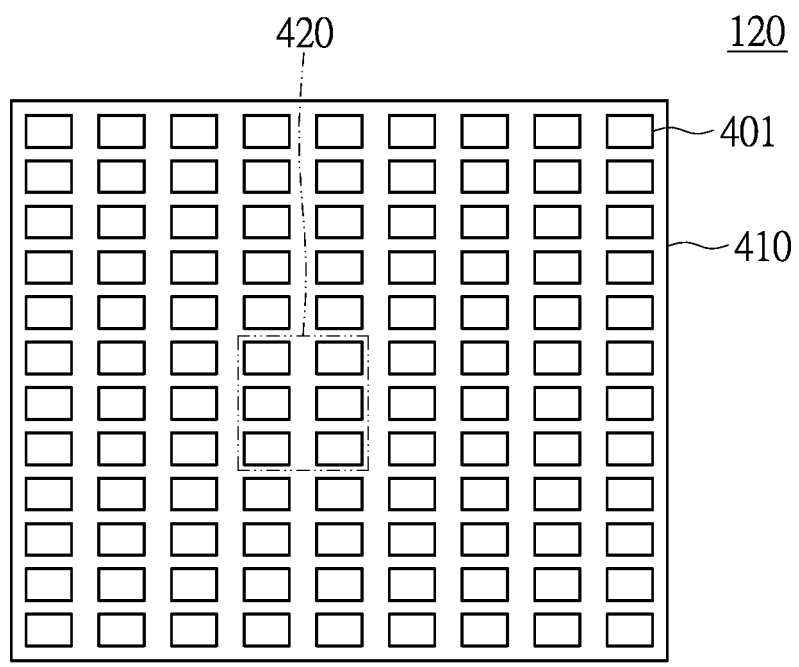
FIG. 4A is a schematic diagram illustrating the structure of one embodiment of the photoelectric sensor of the present disclosure.

Please refer to FIG. 1 and FIG. 4A together, wherein FIG. 4A is a schematic diagram illustrating the structure of one embodiment of the photoelectric sensor of the present disclosure. The photoelectric sensor 120 has a sensing array 410 disposed below the fingerprint sensing surface FS, and a part of the sensing array 410 is set as a spectrum sensing region 420. The sensing array 410 includes a plurality of photosensitive units 401, and the plurality of photosensitive units 401 can be disposed according to the actual requirements and is not limited to the arrangement as shown in FIG. 4A. The spectrum sensing region 420 includes one or more photosensitive units 401 and can be disposed according to the actual requirements and is not limited to the center of the sensing array 410.

In the first sensing mode, the identification unit 110 senses the finger 201 by using the entire sensing array 410 of the photoelectric sensor 120 to obtain a fingerprint image. In the second sensing mode, the identification unit 110 senses the spectrum information by using the plurality of photosensitive units 401 disposed in the spectrum sensing region 420 of the sensing array 410 of the photoelectric sensor 120 to determine the blood glucose information. In other words, the plurality of photosensitive units 401 in the sensing array 410 can be used in both the first and second sensing modes, the identification unit 110 can select the electronic signals outputted by the plurality of photosensitive units 401 to sense and analyze according to the actual requirements, and the selection of the spectrum sensing region 420 depends on the signal source from a hardware circuit or system software. The present disclosure does not limit thereto.

Figure 4B:
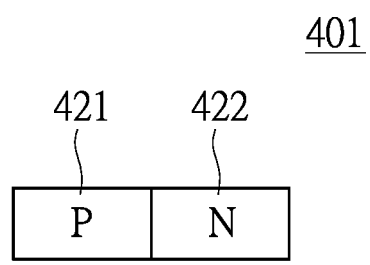
FIG. 4B is a schematic diagram illustrating the structure of one embodiment of the photosensitive unit of the present disclosure.

Please refer to FIG. 4B which is a schematic diagram illustrating the structure of one embodiment of the photosensitive unit of the present disclosure. The photosensitive unit 401 includes a first type doped semiconductor layer 421 (P-type) and a second type doped semiconductor layer 422 (N-type), wherein the two doped semiconductor layers form together a PN interface. The first type doped semiconductor layer 421 and the second type doped semiconductor layer 422 may be made of silicon including one of single crystal silicon, polycrystal silicon, amorphous silicon and microcrystal silicon. The semiconductor material may be $CuInGaSe_2$ (CIGS), CdS, CdSe, GaAs, InGaAs, InP, CuInSe2 (CIS), CdTe, InP, and semiconductor organic material, or a multi-layered structure stacked by a combination thereof. Material of the photoelectric sensor 120 is not limited thereto. The N-type dopant doped in the silicon semiconductor material may be an element of group V listed in the Periodic Table, and the P-type dopant doped in the silicon semiconductor material may be an element of group III listed in the Periodic Table, wherein the element of group V includes P, As, Sb, and so on, and the element of group III includes B, Al, Ga, In, and so on.

The plurality of photosensitive units 401 made of different materials can sense the light intensity signal having a specific waveband. For example, a sensor made of Indium Gallium Arsenide (InGaAs) has a sensing waveband ranging from 800 nm-2600 nm, a photodiode made of silicon has a sensing waveband ranging from 350 nm-1100 nm, and one made of Pbs has a sensing waveband ranging from 1000 nm-3500 nm. The photosensitive units 401 of the present disclosure are not limited thereto.

The sensing array 410 is formed of the plurality of photosensitive units 401, and the plurality of photosensitive units 401 may be made of a single material or different materials according to the desired wavelength range. The sensing array 410 made of a plurality of semiconductor elements having the same waveband is adapted to a fingerprint identification apparatus. In other words, the photoelectric sensor 120 of the present disclosure is adapted to a photoelectric fingerprint identification apparatus, but is not limited thereto. In the present embodiment, one photoelectric sensor 120 may include one or more sensing arrays 410 for sensing a fingerprint image and blood glucose information.

Figure 5:
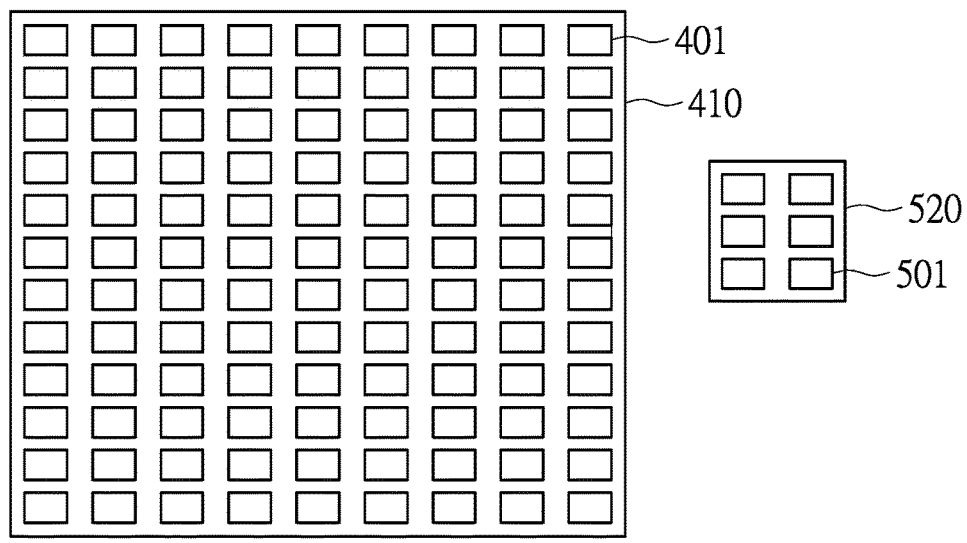
FIG. 5 is s schematic diagram illustrating the structure of the other embodiment of the photoelectric sensor of the present disclosure.

Please refer to FIG. 5 which is a schematic diagram illustrating the structure of another embodiment of the photoelectric sensor of the present disclosure. The photoelectric sensor 120 includes the sensing array 410 and a spectrum sensing element 520, wherein the sensing array 410 includes the plurality of photosensitive units 401, and the spectrum sensing element 520 includes a plurality of photosensitive units 501. The difference between FIG. 5 and FIG. 4A is in the spectrum sensing element 520 shown in FIG. 5. The sensing array 410 is used to sense the fingerprint image and the spectrum sensing element 520 is used to sense the spectrum information. The spectrum sensing element 520 is disposed around the sensing array 410, wherein the spectrum sensing element 520 is an independent element and does not belong to a part of the sensing array 410. For the structure of the plurality of photosensitive units 401 shown in FIG. 5 refer to FIG. 4B, and unnecessary details are not repeated herein.

In the process of sensing, the fingerprint identification apparatus 100 obtains the fingerprint image and spectrum information by means of the first and second sensing modes, wherein the fingerprint image is used to verify the user's fingerprint and the spectrum information is used to recognize the user's biometric signals. By using the biometric signals obtained from the spectrum information, the fingerprint identification apparatus 100 can identify whether the finger is real or not, and the fingerprint is used to connect to the user data. When the finger is determined to be a fake finger, it can choose to stop the sensing mode or to stop recording the sensed information.

Figure 6:
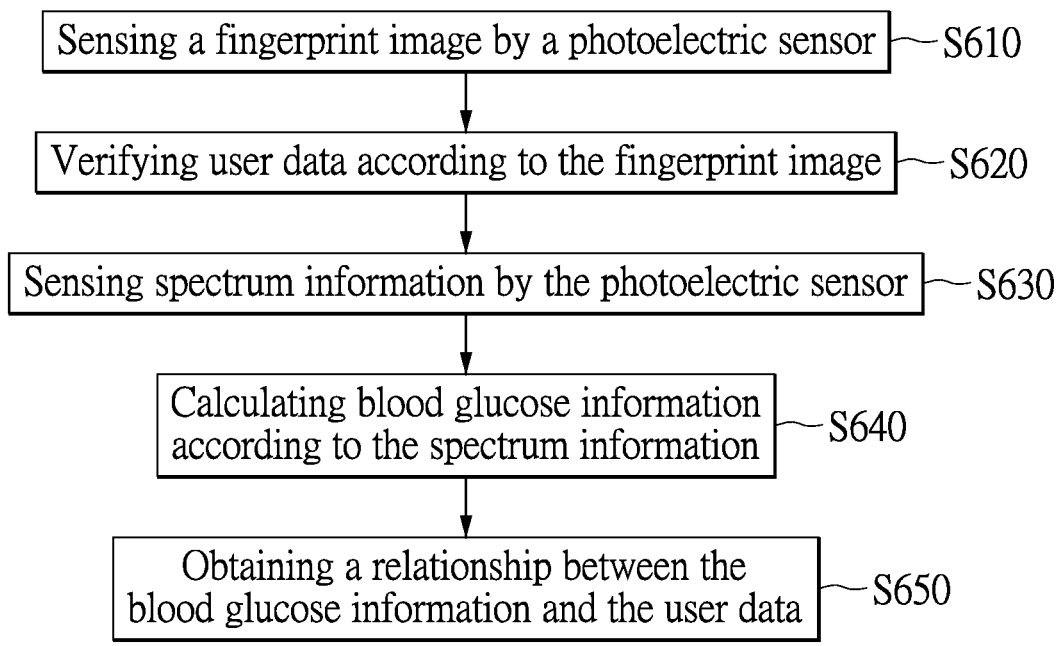
FIG. 6 is a flow chart of one embodiment of the biometric signals sensing method of the present disclosure.

Please refer to FIG. 1 and FIG. 6 together, wherein FIG. 6 is a flow chart of one embodiment of the biometric signals sensing method of the present disclosure. The steps are as follows. S601: sensing a fingerprint image by using the photoelectric sensor 120; S620: verifying user data according to the fingerprint image; S630: sensing spectrum information by using the photoelectric sensor 120; S640: calculating blood glucose information through the spectrum information; and S650: obtaining a relationship between the blood glucose information and the user data.

After the fingerprint identification apparatus 100 obtains the spectrum information, it can identify whether the finger 201 is real or not. The identification method is to sense whether the finger 201 has an absorption peak of a water molecule. In addition, in S630, the fingerprint identification apparatus 100 provides the test light LS having different spectra to sense the finger 201, and the test light LS can be generated on or below the finger 201 to sense the absorption spectrum with respect to the test light LS transmitting or reflected off of the finger 201. After that, the absorption spectrum is used to sense biometric signals such as blood glucose.

In summary, the fingerprint identification apparatus 100 of the present disclosure can simultaneously sense fingerprint images and biometric signals, that is, it can identify whether the finger 201 is real or not and sense blood glucose information without using the invasive measurement method at the same time. In addition, the present disclosure can verify the obtained fingerprint image and compare the biometric signals with the user data to obtain the relationship therebetween, thereby effectively promoting usability and saving operation time.

The above-mentioned descriptions represent merely the exemplary embodiment of the present disclosure, without any intention to limit the scope of the present disclosure thereto. Various equivalent changes, alterations or modifications based on the claims of present disclosure are all consequently viewed as being embraced by the scope of the present disclosure.

What is claimed is:

1. A fingerprint identification apparatus adapted to sense fingerprint images in a first sensing mode and blood glucose information in a second sensing mode, comprising:
    at least one light module for generating a test light projected to a finger so as to generate first light intensity signals in a first sensing mode or second light intensity signals in a second sensing mode;
    at least one photoelectric sensor having a fingerprint sensing face adapted for placement of a finger, and including:
        a sensing array configured to:
            receive the first light intensity signals in the first sensing mode;
            convert the first light intensity signals into first electronic signals in the first sensing mode; and
        a spectrum sensing element configured to:
            receive the second light intensity signals in the second sensing mode; and
            convert the second light intensity signals into second electronic signals in the second sensing mode; and
    an identification unit electrically connected with the photoelectric sensor and configured to:
        receive the first electronic signals in the first sensing mode;
        generate a fingerprint image in the first sensing mode according to the first electronic signals;
        receive the second electronic signals in the second sensing mode;
        generate a piece of spectrum information according to the second electronic signals; and
        obtain a piece of blood glucose information according to the spectrum information in the second mode.

2. The fingerprint identification apparatus according to claim 1, wherein the light module is disposed in the vicinity of the photoelectric sensor.

3. The fingerprint identification apparatus according to claim 1, wherein the light module is disposed above and spaced apart from the photoelectric sensor so that the finger is disposed between the photoelectric sensor and the light module.

4. The fingerprint identification apparatus according to claim 1, wherein the light module comprises a plurality of light sources having different wavelength ranges for generating the test light, and the test light has a wavelength range ranging from 700 nm-3000 nm.

5. The fingerprint identification apparatus according to claim 1, wherein the light module comprises the plurality of light sources and a plurality of filters, and the plurality of filters are respectively disposed on the plurality of light sources for producing a spectrum having different wavebands.

6. The fingerprint identification apparatus according to claim 1, wherein in the second sensing mode, the light module sequentially generates the test light having different wavelength ranges, and the test light has a wavelength range ranging from 700 nm-3000 nm.

7. The fingerprint identification apparatus according to claim 1, wherein the sensing array and the spectrum sensing element are disposed below the fingerprint sensing face, the sensing array and the spectrum sensing element each includes a plurality of photosensitive units, and the photosensitive units of the sensing array and the photosensitive units of the spectrum sensing element are arranged in the same matrix.

8. The fingerprint identification apparatus according to claim 1, wherein the sensing array and the spectrum sensing element each includes a plurality of photosensitive units, and the photosensitive units of the sensing array and the photosensitive units of spectrum sensing element are respectively arranged in two matrixes.

9. The fingerprint identification apparatus according to claim 1, wherein the identification unit is configured to verify user data according to the fingerprint image, and then determines that the blood glucose information corresponds to the user data in response to verifying that the user data corresponds to the fingerprint image.

10. The fingerprint identification apparatus according to claim 1, wherein the fingerprint identification apparatus determines whether the spectrum information includes an absorption peak of glucose and an absorption peak of bone to verify the finger is a real finger or a fake finger.

11. The fingerprint identification apparatus according to claim 1, wherein the sensing array is formed of a plurality of photosensitive units, and each of the plurality of photosensitive units comprises a first type doped semiconductor layer and a second type doped semiconductor layer.

12. The fingerprint identification apparatus according to claim 1, wherein the identification unit comprises:
   an analog/digital converter electrically connected to the photoelectric sensor for receiving the first electronic signals or the second electronic signals outputted by the photoelectric sensor and converting the first electronic signals or the second electronic signals into digital signals, and
   a processing unit electrically connected to the analog/digital converter and receiving the digital signals to output the fingerprint image in the first sensing mode or calculate the blood glucose information in the second sensing mode.

13. The fingerprint identification apparatus according to claim 1, further comprising a light controller electrically connected to the light module for controlling spectrum of the test light.

14. A biometric signals sensing method adapted to fingerprint identification apparatus, comprising:
   providing, by at least one light module, a test light projected to a finger so as to generate first light intensity signals in a first sensing mode or second light intensity signals in a second sensing mode;
   receiving and converting, by a sensing array of a photoelectric sensor, the first light intensity signals into first electronic signals in the first sensing mode;
   obtaining, by an identification unit, a fingerprint image according to the first electronic signals in the first sensing mode;
   verifying, by the identification unit, user data according to the fingerprint image;
   receiving and converting, by a spectrum sensing element of the photoelectric sensor, the second light intensity signals into second electronic signals in the second mode;
   obtaining, by the identification unit, spectrum information according to the second electronic signals in the second mode;
   analyzing and calculating, by the identification unit, the spectrum information to obtain blood glucose information; and
   determining, by the identification unit, that the blood glucose information corresponds to the user data in response to verifying that the user data corresponds to the fingerprint image.

15. The biometric signals sensing method according to claim 14, further comprising: determines whether the spectrum information includes an absorption peak of glucose and an absorption peak of bone to verify a sensed finger is a real finger or a fake finger.

16. The biometric signals sensing method according to claim 14, wherein in the step of obtaining the spectrum information further comprises: providing the test light having different spectra to the finger, wherein the test light is generated on or below the finger.

* * * * *